United States Patent [19]
Lutz et al.

[11] Patent Number: 5,650,527
[45] Date of Patent: Jul. 22, 1997

[54] PREPARATION OF AMIDO ESTER COMPOUNDS

[75] Inventors: Gary Paul Lutz, Church Hill; George Chester Zima, Kingsport, both of Tenn.; William Charles Dickason, Batesville, Ark.

[73] Assignee: Eastman Chemical Company, Kingsport, Tenn.

[21] Appl. No.: 464,438

[22] Filed: Jun. 5, 1995

[51] Int. Cl.$^6$ .................................................. C07C 231/00
[52] U.S. Cl. ................................ 554/68; 554/45; 554/69
[58] Field of Search .................................. 554/45, 68, 69

[56] References Cited

FOREIGN PATENT DOCUMENTS 0 355 384 A1  7/1989  European Pat. Off. ...... C07C 309/42

OTHER PUBLICATIONS

Cabaret et al, Synthesis, vol. 5, pp. 480–482, 1994.

*Primary Examiner*—Deborah D. Carr
*Attorney, Agent, or Firm*—John D. Thallemer; Harry J. Gwinnell

[57] ABSTRACT

This invention relates to a process for preparing amido ester compounds. The process involves (I) forming a mixture in a reactor of a phenol derivative and an amido-carboxylic acid at a temperature which ensures at least partial solubility of the phenol derivative and the amido-carboxylic acid, and (II) adding a carboxylic anhydride incrementally to the mixture formed in Step (I) while distilling a by-product carboxylic acid from the reactor. The amido esters are useful as bleach activators.

14 Claims, No Drawings

PREPARATION OF AMIDO ESTER COMPOUNDS

FIELD OF THE INVENTION

This invention relates to a process for preparing amido ester compounds from a phenol derivative, an amido-carboxylic acid and a carboxylic anhydride.

BACKGROUND OF THE INVENTION

Direct esterification of carboxylic acids with phenols substituted with electron withdrawing groups is not typically possible due to the deactivation effect that the electron withdrawing group has on the phenolic oxygen. Methods to overcome this deactivation effect include activating the carboxylic acid by converting it into a carboxylic acid chloride or a carboxylic anhydride. Carboxylic acids can be converted to carboxylic anhydrides by reacting the carboxylic acid with a lower carboxylic anhydride, such as acetic anhydride, at elevated temperatures. However, this method suffers from high cost and volume of waste associated with producing and using acid chlorides, or the higher cost of the additional steps required to prepare carboxylic anhydrides other than acetic anhydride. Additionally, the carboxylic acid to be activated cannot contain reactive functional groups such as alcohols, thiols, amines, and amides since such functional groups are known to react with anhydrides to form undesirable side products.

European Patent EP 0 355 384 A1 discloses a process for preparing acyloxybenzenesulfonic acid or its salt by reacting hydroxybenzenesulfonic acid and a carboxylic acid in the presence of acetic anhydride. Acetic acid is removed continuously from the reaction. The carboxylic acid is a hydrocarbon which does not contain any reactive functional groups other than the primary carboxylic acid group which reacts with acetic anhydride.

Another method to overcome the deactivation effect of an electron withdrawing group on a phenolic oxygen is to first acylate a phenol with a low molecular weight anhydride, such as acetic anhydride, and then perform a transesterification reaction with the acylated phenol and a carboxylic acid. The disadvantage associated with this method is the additional steps required to produce the acylated phenol. U.S. patent application Ser. No. 08/294,236 discloses a five step method for preparing a purified alkali metal salt of 4-sulfophenyl-[(1-oxyalkanoyl)amino]alkanoate wherein an acylated phenol intermediate is formed.

Accordingly what is needed is a process to prepare amido ester compounds, which have perborate-activating properties, without the necessity of preforming an acylated phenol intermediate. In addition, the process to prepare amido ester compounds should avoid the formation of undesirable side products.

SUMMARY OF THE INVENTION

The present invention is directed to a process for preparing an amido ester compound having a formula selected from the group consisting of

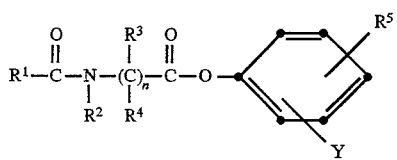

and

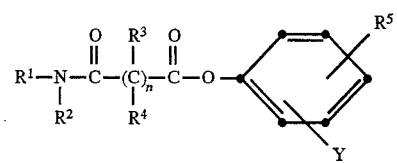

said process comprising the following steps:
(I) forming a mixture in a reactor of a phenol derivative having the formula

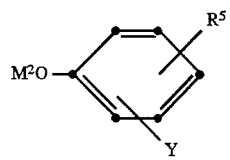

and an amido-carboxylic acid having a formula selected from the group consisting of

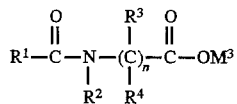

and

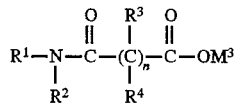

at a temperature which ensures at least partial solubility of the phenol derivative and the amidocarboxylic acid, and
(II) adding a carboxylic anhydride incrementally to the mixture formed in Step (I) while distilling a by-product carboxylic acid from the reactor, said carboxylic anhydride having a formula

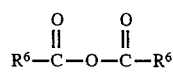

provided that the phenol derivative, amido-carboxylic acid and carboxylic anhydride are in a molar ratio of 1:0.9–5.0:0.5–1.5;
wherein $M^1$, $M^2$ and $M^3$ are independently selected from the group consisting of hydrogen and an alkali metal atom; $R^1$ is selected from the group consisting of an alkyl, alkenyl, alkynyl, or cycloalkyl group having 1 to 26 carbon atoms, and an aryl or alkylaryl group having 6 to 14 carbon atoms; $R^2$ is selected from the group consisting of hydrogen, an alkyl, alkenyl, alkynyl, or cycloalkyl group having 1 to 10 carbon atoms, and an aryl or alkylaryl group having 6 to 10 carbon atoms; $R^3$ and $R^4$ are independently selected from the group consisting of hydrogen, an alkyl, alkenyl, alkynyl, or cycloalkyl group having 1 to 10 carbon atoms, and an aryl or alkylaryl group having 6 to 10 carbon atoms; $R^5$ is selected from the group consisting of hydrogen, halogen, and alkyl, alkenyl, alkynyl, cycloalkyl, or alkoxy group having 1 to 6 carbon atoms; $R^6$ is selected from the group consisting of an alkyl, alkenyl, alkynyl, or cycloalkyl group having 1 to 10 carbon atoms and an aryl or alkylaryl group having 6 to 10 carbon atoms; Y is selected from the group consisting of $SO_3M^1$, $OSO_3M^1$, $(CH_2)_mSO_3M^1$, $(CH_2)_mOSO_3M^1$, $CO_2M^1$, and $N(R^7)_3X$; $R^7$ is selected from the group consisting of an alkyl group having 1 to 6 carbon atoms and a cycloalkyl group having 4 to 6 carbon atoms; X is a halogen atom; n is an integer from 1 to 10; and m is an integer from 1 to 2. The amido ester compounds possess perborate-activating properties.

DESCRIPTION OF THE INVENTION

The process of the present invention is used to prepare an amido ester compound. The amido ester compound either has the formula

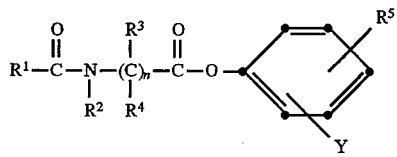

or the amido ester compound has the formula

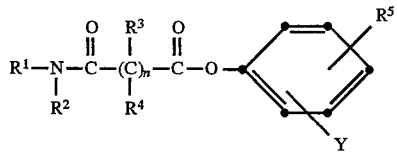

In the above amido ester formulas, $R^1$ is selected from an alkyl, alkenyl, alkynyl, or cycloalkyl group having 1 to 26 carbon atoms, or an aryl or alkylaryl group having 6 to 14 carbon atoms. $R^2$ is selected from hydrogen, or an alkyl, alkenyl, alkynyl, or cycloalkyl group having 1 to 10 carbon atoms, or an aryl or alkylaryl group having 6 to 10 carbon atoms. $R^3$ and $R^4$ are independently selected from hydrogen, or an alkyl, alkenyl, alkynyl, or cycloalkyl group having 1 to 10 carbon atoms, or an aryl or alkylaryl group having 6 to 10 carbon atoms. $R^5$ is selected from hydrogen, halogen, and alkyl, alkenyl, alkynyl, cycloalkyl, or alkoxy group having 1 to 6 carbon atoms. The letter n is an integer from 1 to 10. Y is selected from $SO_3M^1$, $OSO_3M^1$, $(CH_2)_mSO_3M^1$, $(CH_2)_mOSO_3M^1$, $CO_2M^1$, and $N(R^7)_3X$. In the definition of Y, $M^1$ is hydrogen or an alkali metal atom. $R^7$ is selected from an alkyl group having 1 to 6 carbon atoms or a cycloalkyl group having 4 to 6 carbon atoms. X is a halogen atom, and m is an integer from 1 to 2. Preferably, the amido ester compound is selected from sodium 4-sulfophenyl-6-[(1-oxyoctyl)amino]hexanoate, sodium 4-sulfophenyl-6-[(1-oxynonyl)amino]hexanoate, sodium 4-sulfophenyl-6-[(1-oxydecyl)amino]hexanoate, and sodium 4-sulfophenyl-6-[(2-ethyl-1-oxyhexyl)amino]hexanoate.

The process for preparing the amido ester compound may involve one or two steps depending on the state of the reactants. Step (I) involves forming a mixture in a reactor of a phenol derivative and an amido-carboxylic acid. Optionally, a catalyst and a reaction solvent are included in Step (I). In cases where a reaction solvent is not added to Step (I), the amido-carboxylic acid serves to make the reaction fluid. The phenol derivative has the formula:

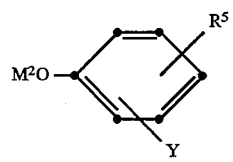

In the above formula for the phenol derivative, $R^5$ is selected from hydrogen, halogen, and alkyl, alkenyl, alkynyl, cycloalkyl, or alkoxy group having 1 to 6 carbon atoms. Preferably $R^5$ is a hydrogen, chlorine or bromine. Y is selected from $SO_3M^1$, $OSO_3M^1$, $(CH_2)_mSO_3M^1$, $(CH_2)_mOSO_3M^1$, $CO_2M^1$, and $N(R^7)_3X$. Preferably, Y is $SO_3M^1$, $OSO_3M^1$, and $CO_2M^1$. In the definition of Y, $M^1$ and $M^2$ are independently hydrogen or an alkali metal atom, preferably $M^1$ is sodium and $M^2$ is hydrogen. $R^7$ is selected from an alkyl group having 1 to 6 carbon atoms or a cycloalkyl group having 4 to 6 carbon atoms. X is a halogen atom, and m is an integer from 1 to 2. Preferably the phenol derivative is sodium 4-hydroxybenzenesulfonate.

The amido-carboxylic acid or alkali metal salt thereof has either the formula

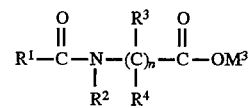

or the amido-carboxylic acid or alkali metal salt thereof has the formula

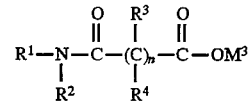

In the above formula for the amido-carboxylic acid, R1, R2, R3, R4, and the letter n are as defined above, and $M^3$ is selected from a hydrogen atom or an alkali metal atom. The amido-carboxylic acid contains a carboxylic acid portion and an amino-carboxylic acid portion which are joined by an amide linkage. Preferred amido-carboxylic acids are 6-[(1-oxyoctyl)amino]hexanoic acid, 6-[(1-oxynonyl)amino]hexanoic acid, 6-[(1-oxydecyl)amino]hexanoic acid, 6-[(2-ethyl-1-oxyhexyl)amino]hexanoic acid, N-heptyladipamic acid, N-octyladipamic acid, N-nonyladipamic acid, N-decyladipamic acid, N-heptylpimelamic acid, N-octylpimelamic acid, N-nonylpimelamic acid, N-decylpimelamic acid, N-heptylsuberamic acid, N-octylsuberamic acid, N-nonylsuberamic acid, and N-decylsuberamic acid. Mixtures of amido-carboxylic acids may also be used.

The phenol derivative and amido-carboxylic acid are combined at a temperature which ensures at least partial solubility of the phenol derivative and the amido-carboxylic acid.

Step (II) involves adding a carboxylic anhydride incrementally to the mixture formed in Step (I). The term incrementally implies a series of regular consecutive additions including both continuous and intermittent additions of the carboxylic anhydride. The carboxylic anhydride has the formula:

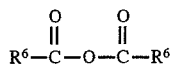

In the above formula for the carboxylic anhydride, $R^6$ is independently selected from an alkyl, alkenyl, alkynyl, or cycloalkyl group having 1 to 10 carbon atoms, preferably, 1 to 3 carbon atoms, or an aryl or alkylaryl group having 6 to 10 carbon atoms. Examples of suitable carboxylic anhydrides are: acetic anhydride, propionic anhydride, butyric anhydride, and isobutyric anhydride. Preferably, the carboxylic anhydride is acetic anhydride. Mixtures of carboxylic anhydrides can also be used.

The carboxylic anhydride is added to a stirring mixture of the phenol derivative and the amido-carboxylic acid over 5 minutes to 5 hours at a temperature of 100° C. to 220° C. Preferably the addition of the carboxylic anhydride is accomplished over 15 minutes to 2 hours. The rate of addition of the carboxylic anhydride is dependent upon the rate at which all of the anhydride species react with the phenol derivative. If the carboxylic anhydride addition rate exceeds the rate at which all of the anhydride species react with the phenol derivative, side reactions leading to undesired impurities are accelerated. Temperatures above 220° C. are not recommended due to acceleration of color forming side reactions. The reaction is maintained at a pressure which ensures that the by-product carboxylic acid will distill from the reactor for 0.1 to 10 hours after the addition of carboxylic anhydride is complete. Preferably, the reaction temperature is maintained at 120° C. to 180° C. and at a pressure which ensures that the by-product carboxylic acid will distill from the reactor for 0.5 to 6.0 hours after the addition of carboxylic anhydride is completed.

The amido-carboxylic acid is present in an amount of 0.9 to 5 moles per mole of the phenol derivative, preferably 0.95 to 2 moles per mole of the phenol derivative. An excess of amido-carboxylic acid relative to the amount of phenol derivative is preferred in cases where a reaction solvent is not added to Step (I). The carboxylic anhydride is present in an amount of 0.5 to 1.5 moles per mole of the phenol derivative, preferably from 0.8 to 1.2 moles. It is desirable to use nearly a stoichiometric amount of carboxylic anhydride relative to the limiting reagent, either amido-carboxylic acid or phenol derivative, plus enough additional carboxylic anhydride to react with any water which may be present in the reactor. Water may enter the reactor in low levels with the starting materials or with a reaction solvent.

The reaction of the amido-carboxylic acid with the carboxylic anhydride to form both a mixed anhydride and amido-carboxylic acid anhydride can be extremely rapid at elevated temperatures. It is important to meter the addition of the carboxylic anhydride under conditions which will ensure that only low concentrations of mixed anhydride and amido-carboxylic acid anhydride are generated. Since it is known that an amido-carboxylic acid can polymerize in the presence of carboxylic anhydride, the rate of reaction of carboxylic anhydride, mixed anhydride, and amido-carboxylic acid anhydride with the phenol derivative should be equal to or greater than the rate of addition of carboxylic anhydride thereby ensuring that a high concentration of mixed anhydride or amido-carboxylic acid anhydride never develops.

An esterification and/or transesterification catalyst is preferably added to the mixture prepared in Step (I). The catalyst increases the rate of esterification and transesterification reactions and may improve conversion of reactants and yield of the amido ester product. Esterification and transesterification catalysts are known in the art. For example, such catalysts include: tertiary amines, alkali metal salts of carboxylic acids, phase transfer catalysts, aromatic amine catalysts, and Lewis acid catalysts. Preferred catalysts for use in the process are: dimethyl aminopyridine, imidazole, sodium acetate, sodium hydroxide, tetrabutyl ammonium bromide, and titanium tetraisopropoxide. More preferably, the catalyst is sodium acetate. Combinations of catalysts can also be used. A preferred combination of catalysts is sodium acetate and imidazole. Each catalyst used in the process is present in an amount of 0.005 to 0.3 mole per mole of the phenol derivative, preferably 0.01 to 0.15 moles.

Optionally, a reaction solvent can be added to the process for the preparation of the amido ester compounds. Reaction solvents which will not react with the amido-carboxylic acid or the carboxylic anhydride and have boiling points higher than, or form azeotropes with, the by-product carboxylic acid, may be combined in Step (I) with the phenol derivative and amido-carboxylic acid. Useful reaction solvents include polar aprotic solvents such as N,N-dimethylacetamide, dialkyl sulfoxide wherein the alkyl group has one to six carbon atoms such as dimethyl sulfoxide, dimethyl ethers of diethylene glycol such as triglyme, cyclic or acyclic alkyl sulfone wherein the alkyl group has one to six carbon atoms such as tetrahydrothiophene-1,1-dioxide (also known as tetramethylene sulfone or sulfolane), and halogenated aromatic solvents such as dichlorobenzene and trichlorobenzene. Polar aprotic reaction solvents for use in this process also include less polar aprotic solvents such as alkyl or alkoxy substituted aromatic solvents where the alkyl or alkoxy group contains one to six carbon atoms such as triisopropylbenzene and dimethoxybenzene. Preferably, the reaction solvent is tetrahydrothiophene-1,1-dioxide. A mixture of reaction solvents may also be used. If used, the reaction solvent is present in an amount of 2 to 50 moles per mole of the phenol derivative. Preferably, the reaction solvent is present in an amount of 5 to 20 moles per mole of the phenol derivative.

The degree of conversion of the amido-carboxylic acid and phenol derivative into the amido ester product is controlled by varying the time that the reaction is held at reaction conditions while removing by-product carboxylic acid after the carboxylic anhydride addition is complete. After sufficient by-product carboxylic acid has been removed from the reactor, crude amido ester product remains. The crude amido ester product contains amido ester, unreacted starting materials, impurities and reaction solvent. Reaction solvent can be removed by such methods as crystallization/filtration or by direct evaporation.

The amido ester product can be further purified, as necessary, by methods known in the art. Such methods include recrystallization, reslurry, digestion, and washing with a purification solvent. The purification solvent can be selected from a wide variety of solvents such as nonpolar hydrocarbon solvents, polar protic solvents, and polar aprotic solvents. Preferred purification solvents include acetic acid, propionic acid, methyl acetate, methyl propionate, methanol, ethanol, propanol, and dimethyl acetamide. In addition, the reaction solvent used in Step (I) of the process may also be used as a purification solvent.

If the process is operated under low conversion conditions, the recycle of unreacted starting materials into Step (I) makes the process more economically attractive. Even if the process is operated at high conversion conditions, recycling unreacted starting materials into Step (I) will improve the yield of amido ester product. The process can be operated in a batchwise or continuous fashion. It may be advantageous, for example, for control purposes, to divide Step (II) into two or more distinctive stages such that the addition of carboxylic anhydride occurs in one or more initial stages followed by one or more distillation stages which remove by-product carboxylic acid.

The process of the present invention will be further illustrated by a consideration of the following examples, which are intended to be exemplary of the invention. All parts and percentages in the examples are on a weight basis unless otherwise stated.

Examples 1–3 represent experiments using excess acetic anhydride under a variety of conditions.

EXAMPLE 1

To a stirring mixture of 25.0 gram (0.127 mole) of sodium 4-hydroxybenzenesulfonate, 32.0 gram (0.118 mole) of 6-[(1-oxynonanoyl)amino]hexanoic acid, 0.43 gram (6.3 mmole) of imidazole, 0.50 gram (6.1 mmole) of sodium acetate, and 180 gram (1.5 mole) of sulfolane at 170° C. and at 40 mm of Hg absolute, was added 15.4 gram (0.151 mole) of acetic anhydride over a 1 hour period. The acetic anhydride was added below the surface of the stirring reaction mixture. Under the above conditions, sulfolane was refluxing at the top of a 15" distillation column. The reaction mixture was allowed to stir for 30 minutes after the addition of the acetic anhydride was complete.

The pressure was gradually lowered to cause the sulfolane to distill from the reactor. The sulfolane distilled off over 1.5 hours. The reactor was cooled to room temperature and the crude solids (70.0 gram) were transferred to a vacuum oven. The solids were allowed to dry at 110° C. and at 28 inches of vacuum for approximately 20 hours to afford 51.0 gram light tan solids. HPLC data is summarized in Table I.

EXAMPLE 2

A stirring mixture of 21.8 gram (0.111 mole) of sodium 4-hydroxybenzenesulfonate, 30.0 gram (0.111 mole) of 6-[(1-oxynonanoyl)amino]hexanoic acid, 0.36 gram (5.3 mmole) of imidazole, 0.43 gram (5.2 mmole) of sodium acetate, 160 gram (1.3 mole) of sulfolane, and 32.4 gram (0.317 mole) of acetic anhydride at 25° C. and at 40 mm of Hg absolute was allowed to warm from 25° C. to 170° C. over 40 minutes. Low boiling materials were allowed to distill from the reactor throughout the reaction.

The reaction mixture was stirred for 50 minutes after the temperature reached 170° C. Under the above conditions, sulfolane was refluxing at the top of a 15" distillation column. The pressure was then gradually lowered to cause the sulfolane to distill from the reactor. The sulfolane distilled off over 1.5 hours. The reactor was cooled to room temperature and the crude solids (50.3 gram) were transferred to a vacuum oven. The solids were allowed to dry at 155° C. and at 28 inches of vacuum for approximately 20 hours to afford 45.0 gram light tan solids. HPLC data is summarized in Table I.

EXAMPLE 3

A stirring mixture of 21.8 gram (0.111 mole) of sodium 4-hydroxybenzenesulfonate, 30.0 gram (0.111 mole) of 6-[(1-oxynonanoyl)amino]hexanoic acid, 0.36 gram (5.3 mmole) of imidazole, 0.43 gram (5.2 mmole) of sodium acetate, 160 gram (1.3 mole) of sulfolane, and 32.4 gram (0.317 mole) of acetic anhydride at 25° C. and at atmospheric pressure was allowed to warm from 25° C. to 170° C. over 30 minutes. The pressure was then lowered to 40 mm of Hg absolute. Low boiling materials were allowed to distill from the reactor throughout the reaction.

The reaction mixture was allowed to stir for 2 hours after the pressure was reduced to 40 mm of Hg absolute. Under the above conditions, sulfolane was refluxing at the top of a 15" distillation column. The pressure was then gradually lowered to cause the sulfolane to distill from the reactor. The sulfolane distilled off over 1.5 hours. The reactor was cooled to room temperature and most of the crude solids (~48 gram) were transferred to a vacuum oven. Due to the waxy nature of the solids, some of the crude solids were not removed from the reaction flask. The waxy solids were allowed to dry at 115° C. and at 28 inches of vacuum for approximately 20 hours to afford 42.1 gram light brown solids. HPLC data is summarized in Table I.

Examples 4 and 5 represent experiments using a nearly stoichiometric amount of acetic anhydride wherein the acetic anhydride was added in a single aliquot at 25° C. and the reaction mixture was heated to 170° C. in Example 4 at 40 mm of Hg absolute and in Example 5 at atmospheric pressure.

EXAMPLE 4

A stirring mixture of 21.80 gram (0.111 mole) of sodium 4-hydroxybenzenesulfonate, 30.00 gram (0.111 mole) of 6-[(1-oxynonanoyl)amino]hexanoic acid, 0.36 gram (5.3 mmole) of imidazole, 0.43 gram (5.2 mmole) of sodium acetate, 160 gram (1.3 mole) of sulfolane, and 11.9 gram (0.117 mole) of acetic anhydride at 25° C. and at 40 mm of Hg absolute was allowed to warm from 25° C. to 170° C. over 40 minutes. Low boiling materials were allowed to distill from the reactor throughout the reaction.

The reaction mixture was allowed to stir for 2 hours after the reaction mixture temperature reached 170° C. Under the above conditions, sulfolane was refluxing at the top of a 15" distillation column. The pressure was then gradually lowered to cause the sulfolane to distill from the reactor. The sulfolane distilled off over 1.5 hours. The reactor was cooled to room temperature and the crude solids (73.7 gram) were transferred to a vacuum oven. The solids were allowed to dry at 115° C. and at 28 inches of vacuum for approximately 20 hours to afford 45.8 gram light tan solids. HPLC data is summarized in Table I.

EXAMPLE 5

A stirring mixture of 21.8 gram (0.111 mole) of sodium 4-hydroxybenzenesulfonate, 30.0 gram (0.111 mole) of 6-[(1-oxynonanoyl)amino]hexanoic acid, 0.36 gram (5.3 mmole) of imidazole, 0.43 gram (5.2 mmole) of sodium acetate, 160 gram (1.3 mole) of sulfolane, and 11.9 grams (0.117 mole) of acetic anhydride at 25° C. and at atmospheric pressure was allowed to warm from 25° C. to 170° C. over 30 minutes. The pressure was then lowered to 40 mm of Hg absolute. Low boiling materials were allowed to distill from the reactor throughout the reaction.

The reaction mixture was allowed to stir for 2 hours after the pressure was reduced to 40 mm of Hg absolute. Under the above conditions, sulfolane was refluxing at the top of a 15" distillation column. The pressure was then gradually lowered to cause the sulfolane to distill from the reactor. The sulfolane distilled off over 1.5 hours. The reactor was cooled to room temperature and most of the crude solids (59.1 gram) were transferred to a vacuum oven. The solids were allowed to dry at 115° C. and at 28 inches of vacuum for approximately 20 hours to afford 45.3 gram light tan solids. HPLC data is summarized in Table I.

Examples 6 through 12 represent experiments wherein a nearly stoichiometric amount of acetic anhydride was added at a controlled rate at atmospheric pressure while the reactor temperature, catalyst concentration, and anhydride feed rate was varied.

EXAMPLE 6

To a stirring mixture of 21.80 gram (0.1111 mole) of sodium 4-hydroxybenzenesulfonate, 30.0 gram (0.1105 mole) of 6-[(1-oxynonanoyl)amino]hexanoic acid, 0.36 gram (5.3 mmole) of imidazole, 0.43 gram (5.2 mmole) of sodium acetate, and 160.0 gram (1.333 mole) of sulfolane at 170° C. and at atmospheric pressure was added 11.90 gram (0.1166 mole) of acetic anhydride over a 0.9 hour period. The acetic anhydride was added below the surface of the stirring reaction mixture. After the addition of the acetic anhydride was complete, the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours. The reactor was cooled to room temperature and the crude solids (53.6 gram) were transferred to a vacuum oven. The solids were allowed to dry at 150° C. and at 28 inches of vacuum for approximately 20 hours to afford 43.0 gram light tan solids. HPLC data and Hunter Color data are summarized in Table I.

EXAMPLE 7

To a stirring mixture of 21.80 gram (0.1111 mole) of sodium 4-hydroxybenzenesulfonate, 30.0 gram (0.1105 mole) of 6-[(1-oxynonanoyl)amino]hexanoic acid, 0.36 gram (5.3 mmole) of imidazole, 0.43 gram (5.2 mmole) of sodium acetate, and 160.0 gram (1.333 mole) of sulfolane at 145° C. and at atmospheric pressure was added 11.90 gram (0.1166 mole) of acetic anhydride over a 0.75 hour period. The acetic anhydride was added below the surface of the stirring reaction mixture. After the addition of the acetic anhydride was complete, the temperature of the reaction mixture was increased to approximately 170° C. and the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours.

The reactor was cooled to room temperature and the crude solids (66.8 gram) were transferred to a vacuum oven. The solids were allowed to dry at 150° C. and at 28 inches of vacuum for approximately 20 hours to afford 44.6 gram off-white solids. HPLC data and Hunter Color data are summarized in Table I.

EXAMPLE 8

To a stirring mixture of 21.8 gram (0.1111 mole) of sodium 4-hydroxybenzenesulfonate, 30.0 gram (0.1105 mole) of 6-[(1-oxynonanoyl)amino]hexanoic acid, 0.18 gram (2.6 mmole) of imidazole, 0.22 gram (2.7 mmole) of sodium acetate, and 160.0 gram (1.333 mole) of sulfolane at 145° C. and at atmospheric pressure was added 11.90 gram (0.1166 mole) of acetic anhydride over a 1.1 hour period. The acetic anhydride was added below the surface of the stirring reaction mixture. After the addition of the acetic anhydride was complete, the temperature of the reaction mixture was increased to approximately 170° C. and the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours.

The reactor was cooled to room temperature and the crude solids (48.1 gram) were transferred to a vacuum oven. The solids were allowed to dry at 150° C. and at 28 inches of vacuum for approximately 20 hours to afford 46.1 gram off-white solids. HPLC data and Hunter Color data are summarized in Table I.

EXAMPLE 9

To a stirring mixture of 21.80 gram (0.1111 mole) of sodium 4-hydroxybenzenesulfonate, 30.0 gram (0.1105 mole) of 6-[(1-oxynonanoyl)amino]hexanoic acid, 0.36 gram (5.3 mmole) of imidazole, and 160.0 gram (1.333 mole) of sulfolane at 145° C. and at atmospheric pressure was added 11.90 gram (0.1166 mole) of acetic anhydride over a 1.0 hour period. The acetic anhydride was added below the surface of the stirring reaction mixture. After the addition of the acetic anhydride was complete, the temperature of the reaction mixture was increased to approximately 170° C. and the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours.

The reactor was cooled to room temperature and the crude solids (52.4 gram) were transferred to a vacuum oven. The solids were allowed to dry at 150° C. and at 28 inches of vacuum for approximately 20 hours to afford 44.4 gram waxy solids. HPLC data and Hunter Color data are summarized in Table I.

EXAMPLE 10

To a stirring mixture of 21.80 gram (0.1111 mole) of sodium 4-hydroxybenzenesulfonate, 30.00 gram (0.1105 mole) of 6-[(1-oxynonanoyl)amino]hexanoic acid, 0.36 gram (5.3 mmole) of imidazole, 0.43 gram (5.2 mmole) of sodium acetate, and 160.0 gram (1.333 mole) of sulfolane at 145° C. and at atmospheric pressure was added 11.90 gram (0.1166 mole) of acetic anhydride over a 2.0 hour period. The acetic anhydride was added below the surface of the stirring reaction mixture. After the addition of the acetic anhydride was complete, the temperature of the reaction mixture was increased to approximately 170° C. and the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours.

The reactor was cooled to room temperature and the crude solids (48.2 gram) were transferred to a vacuum oven. The solids were allowed to dry at 150° C. and at 28 inches of vacuum for approximately 20 hours to afford 46.2 gram off-white solids. HPLC data and Hunter Color data are summarized in Table I.

EXAMPLE 11

To a stirring mixture of 21.80 gram (0.1111 mole) of sodium 4-hydroxybenzenesulfonate, 30.00 gram (0.1105 mole) of 6-[(1-oxynonanoyl)amino]hexanoic acid, 0.36 gram (5.3 mmole) of imidazole, 0.43 gram (5.2 mmole) of sodium acetate, and 160.0 gram (1.333 mole) of sulfolane at 145° C. and at atmospheric pressure was added 11.90 gram (0.1166 mole) of acetic anhydride over a 0.5 hour period. The acetic anhydride was added below the surface of the stirring reaction mixture. After the addition of the acetic anhydride was complete, the temperature of the reaction mixture was increased to approximately 170° C. and the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours.

The reactor was cooled to room temperature and the crude solids (55.0 gram) were transferred to a vacuum oven. The solids were allowed to dry at 150° C. and at 28 inches of vacuum for approximately 20 hours to afford 45.4 gram off-white solids. HPLC data and Hunter Color data are summarized in Table I.

EXAMPLE 12

To a stirring mixture of 21.80 gram (0.1111 mole) of sodium 4-hydroxybenzenesulfonate, 30.00 gram (0.1105 mole) of 6-[(1-oxynonanoyl)amino]hexanoic acid, 0.36 gram (5.3 mmole) of imidazole, 0.43 gram (5.2 mmole) of sodium acetate, and 160.0 gram (1.333 mole) of sulfolane at 145° C. and at atmospheric pressure was added 11.90 gram (0.1166 mole) of acetic anhydride over a 0.25 hour period. The acetic anhydride was added below the surface of the stirring reaction mixture. After the addition of the acetic anhydride was complete, the temperature of the reaction mixture was increased to approximately 170° C. and the pressure was reduced to 40 mm of Hg absolute, and the reaction mixture was allowed to stir for 2 hours. The pressure was then gradually lowered to cause the sulfolane to distill from the reactor. The sulfolane distilled off over 1.0–1.5 hours.

The reactor was cooled to room temperature and the crude solids (46.2 gram) were transferred to a vacuum oven. The solids were allowed to dry at 150° C. and at 28 inches of vacuum for approximately 20 hours to afford 45.1 gram off-white solids. HPLC data and Hunter Color data are summarized in Table I.

In Table I Impur. 1–3 refer to the following impurities:

Impur. 1

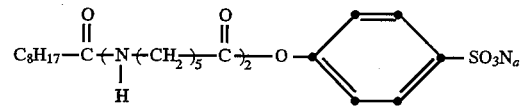

Impur. 2

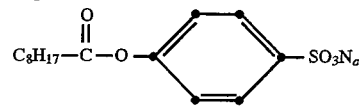

Impur. 3

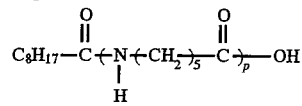

wherein p is >2

The test results in Table I show that the experiments in which all of the anhydride was present at the start of the reaction (Examples 2–5) or in which an excess of anhydride was used (Examples 1–3) resulted in higher levels of Impurity 2 and Impurity 3 than the reactions where a nearly stoichiometric amount of acetic anhydride was added at a controlled rate (Examples 6–12).

Example 6 indicates that the addition of acetic anhydride to the reactor at 170° C. results in higher Hunter color than in Examples 7–12 where the acetic anhydride was added at 145° C. Example 8 indicates that the catalysts can be reduced by 50% with no significant adverse effects on the HPLC assay or Hunter color of the product. Example 9 indicates lower conversion in the absence of sodium acetate.

Amido ester compounds produced by the process of the present invention, without preforming an acylated phenol

TABLE I

HPLC and Hunter Color Analysis (The Samples Were Not Purified)

| Ex. | Prod. (%) | Impur.[1] (%) | Impur.[2] (%) | Amido (%) | Impur.[3] (%) | ABS (%) | SPS (%) | Total (%) | Hunter Color L* | a* | b* |
|---|---|---|---|---|---|---|---|---|---|---|---|
| 1 † | 43.1 | 0.5 | 0.2 | 23.4 | 8.4 | 0 | 31.1 | 106.7 | — | — | — |
| 2 | 75.3 | 1.1 | 3.7 | 0.7 | 3.9 | 5.4 | 1.8 | 91.9 | — | — | — |
| 3 | 61 | 1.2 | 6.4 | 1.1 | 8.8 | 10 | 3.4 | 91.9 | — | — | — |
| 4 | 54.4 | 1.3 | 6.2 | 0.8 | 4.2 | 3.3 | 15.7 | 85.9 | — | — | — |
| 5 † | 81.9 | 1.3 | 1.3 | 4.3 | 4.8 | 0.2 | 7 | 100.8 | — | — | — |
| 6 | 83.3 | 2 | 1.7 | 4.8 | 0 | 1.2 | 1.5 | 94.5 | 69.85 | 4.23 | 12.27 |
| 7 | 91 | 1.4 | 1.5 | 2.1 | 0 | 0.8 | 0.7 | 97.5 | 82.65 | 2.08 | 6.14 |
| 8 | 86.3 | 1.5 | 0.7 | 3.8 | 0 | 3.2 | 0.4 | 95.9 | 87.29 | 1.75 | 6.6 |
| 9 | 68.7 | 4 | 1.2 | 6.1 | 0 | 11.3 | 0.6 | 91.9 | 85.21 | 2.43 | 7.94 |
| 10 | 91.1 | 1 | 0.5 | 2.3 | 0 | 0.8 | 0.4 | 96.1 | 84.17 | 2.69 | 8.16 |
| 11 † | 88.6 | 1 | 0.9 | 1.9 | 0 | 1.7 | 0.4 | 94.5 | 85.52 | 2.21 | 6.99 |
| 12 | 89.8 | 0.9 | 0.6 | 2.7 | 0 | 0.7 | 0.9 | 95.6 | 86.5 | 2.19 | 5.88 |

HPLC assay results are in weight percent.
†Sample also contains diamido-carboxylic acid in 1.6, 0.6, and 0.2 weight percent for Examples 1, 5 and 11, respectively.
Amido = unreacted amido-carboxylic acid.
ABS = 4-acetoxybenzenesulfonic acid sodium salt.
SPS = sodium 4-phenol sulfonate (sodium 4-hydroxybenzenesulfonate).

intermediate, are prepared in good yield, assay, and color by the simultaneous reaction of sodium 4-hydroxybenzenesulfonate and amido-carboxylic acid in the presence of acetic anhydride. Deleterious side reactions leading to undesirable side products have been essentially eliminated by the controlled addition of acetic anhydride into a mixture of sodium 4-hydroxybenzenesulfonate and 6-[(1-oxynonyl)amino]hexanoic acid in sulfolane. In addition, the process uses nearly stoichiometric quantities of reagents which reduces the need to recycle unreacted starting material.

Many variations will suggest themselves to those skilled in this art in light of the above detailed description. All such obvious modifications are within the full intended scope of the appended claims.

What is claimed is:

1. A process for preparing an amido ester compound having a formula selected from the group consisting of

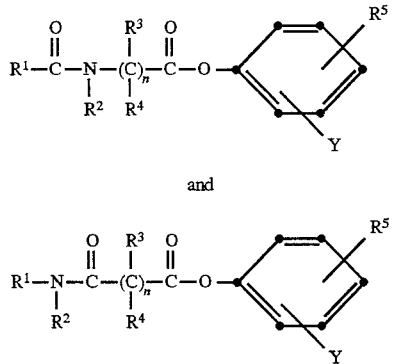

said process comprising the following steps:

(I) forming a mixture in a reactor of a phenol derivative having the formula

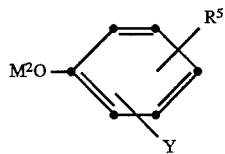

and an amido-carboxylic acid having a formula selected from the group consisting of

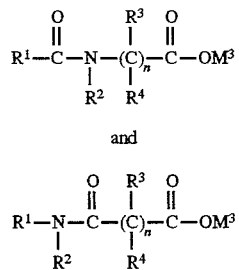

in the presence of a polar aprotic reaction solvent and at least one catalyst, at a temperature of 100° C. to 220° C., and (II) adding a carboxylic anhydride incrementally to the mixture formed in Step (I) while distilling a by-product carboxylic acid from the reactor, said carboxylic anhydride having a formula

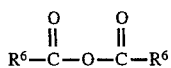

provided that the phenol derivative, amido-carboxylic acid and carboxylic anhydride are in a molar ratio of 1:0.9–5.0:0.5–1.5;

wherein $M^1$, $M^2$ and $M^3$ are independently selected from the group consisting of hydrogen and an alkali metal atom; $R^1$ is selected from the group consisting of an alkyl, alkenyl, alkynyl, or cycloalkyl group having 1 to 26 carbon atoms, and an aryl or alkylaryl group having 6 to 14 carbon atoms; $R^2$ is selected from the group consisting of hydrogen, an alkyl, alkenyl, alkynyl, or cycloalkyl group having 1 to 10 carbon atoms, and an aryl or alkylaryl group having 6 to 10 carbon atoms; $R^3$ and $R^4$ are independently selected from the group consisting of hydrogen, an alkyl, alkenyl, alkynyl, or cycloalkyl group having 1 to 10 carbon atoms, and an aryl or alkylaryl group having 6 to 10 carbon atoms; $R^5$ is selected from the group consisting of hydrogen, halogen, and alkyl, alkenyl, alkynyl, cycloalkyl, or alkoxy group having 1 to 6 carbon atoms; $R^6$ is selected from the group consisting of an alkyl, alkenyl, alkynyl, or cycloalkyl group having 1 to 10 carbon atoms and an aryl or alkylaryl group having 6 to 10 carbon atoms; Y is selected from the group consisting of $SO_3M^1$, $OSO_3M^1$, $(CH_2)_mSO_3M^1$, $(CH_2)_mOSO_3M^1$, $CO_2M^1$ and $N(R^7)_3X$; $R^7$ is selected from the group consisting of an alkyl group having 1 to 6 carbon atoms and a cycloalkyl group having 4 to 6 carbon atoms; X is a halogen atom; n is an integer from 1 to 10; and m is an integer from 1 to 2.

2. The process of claim 1 wherein the carboxylic anhydride is added to a stirring mixture of the phenol derivative and the amido-carboxylic acid over 15 minutes to 2 hours at a temperature of 120° C. to 180° C.

3. The process of claim 1 wherein the phenol derivative is sodium 4-hydroxybenzenesulfonate.

4. The process of claim 1 wherein the amido-carboxylic acid is selected from the group consisting of 6-[(1-oxyoctyl)amino]hexanoic acid, 6-[(1-oxynonyl)amino]hexanoic acid, 6-[(1-oxydecyl)amino]hexanoic acid, 6-[(2-ethyl-1-oxyhexyl)amino]hexanoic acid, and mixtures thereof.

5. The process of claim 1 wherein the amido-carboxylic acid is selected from the group consisting of N-heptyladipamic acid, N-octyladipamic acid, N-nonyladipamic acid, N-decyladipamic acid, N-heptylpimelamic acid, N-octylpimelamic acid, N-nonylpimelamic acid, N-decylpimelamic acid, N-heptylsuberamic acid, N-octylsuberamic acid, N-nonylsuberamic acid, N-decylsuberamic acid, and mixtures thereof.

6. The process of claim 1 wherein the carboxylic anhydride is acetic anhydride.

7. The process of claim 1 wherein the amido ester compound is selected from the group consisting of sodium 4-sulfophenyl-6-[(1-oxyoctyl)amino]hexanoate, sodium 4-sulfophenyl-6-[(1-oxynonyl)amino]hexanoate, sodium 4-sulfophenyl-6-[(1-oxydecyl)amino]hexanoate, and sodium 4-sulfophenyl-6-[(2-ethyl-1-oxyhexyl)amino]hexanoate.

8. The process of claim 1 wherein the polar aprotic reaction solvent is selected from the group consisting of dialkyl sulfoxide wherein the alkyl group has one to six carbon atoms, dimethyl ethers of diethylene glycol such as triglyme, cyclic or acyclic alkyl sulfone wherein the alkyl group has one to six carbon atoms, halogenated aromatic solvents, and alkyl or alkoxy substituted aromatic solvents where the alkyl or alkoxy group contains one to six carbon atoms.

9. The process of claim 8 wherein the reaction solvent is selected from the group consisting of N,N-dimethylacetamide, dimethyl sulfoxide, triglyme, tetrahydrothiophene-1,1-dioxide, dichlorobenzene, trichlorobenzene, triisopropylbenzene, and dimethoxybenzene.

10. The process of claim 9 wherein the reaction solvent is tetrahydrothiophene-1,1-dioxide.

11. The process of claim 1 wherein the catalyst is selected from the group consisting of transesterification catalysts and esterification catalysts.

12. The process of claim 11 wherein the catalyst is selected from the group consisting of alkali metal salts of carboxylic acids, tertiary amines, aromatic amines, and Lewis acids.

13. The process of claim 12 wherein the catalyst is selected from the group consisting of sodium acetate and imidazole.

14. A process for preparing an amido ester compound having a formula selected from the group consisting of

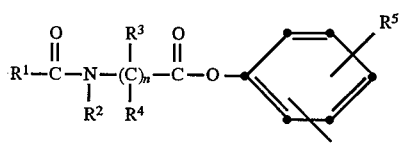

and

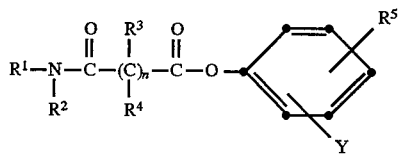

said process comprising the following steps:

(I) forming a mixture in a reactor of a phenol derivative having the formula

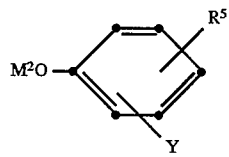

and an amido-carboxylic acid having a formula selected from the group consisting of

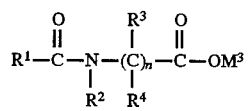

and

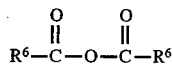

at a temperature of 100° C. to 220° C., and (II) adding a carboxylic anhydride incrementally to the mixture formed in Step (I) while distilling a by-product carboxylic acid from the reactor, said carboxylic anhydride having a formula

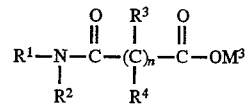

provided that the phenol derivative, amido-carboxylic acid and carboxylic anhydride are in a molar ratio of 1:0.9–5.0:0.5–1.5;

wherein $M^1$, $M^2$ and $M^3$ are independently selected from the group consisting of hydrogen and an alkali metal atom; $R^1$ is selected from the group consisting of an alkyl, alkenyl, alkynyl, or cycloalkyl group having 1 to 26 carbon atoms, and an aryl or alkylaryl group having 6 to 14 carbon atoms; $R^2$ is selected from the group consisting of hydrogen, an alkyl, alkenyl, alkynyl, or cycloalkyl group having 1 to 10 carbon atoms, and an aryl or alkylaryl group having 6 to 10 carbon atoms; $R^3$ and $R^4$ are independently selected from the group consisting of hydrogen, an alkyl, alkenyl, alkynyl, or cycloalkyl group having 1 to 10 carbon atoms, and an aryl or alkylaryl group having 6 to 10 carbon atoms; $R^5$ is selected from the group consisting of hydrogen, halogen, and alkyl, alkenyl, alkynyl, cycloalkyl, or alkoxy group having 1 to 6 carbon atoms; $R^6$ is selected from the group consisting of an alkyl, alkenyl, alkynyl, or cycloalkyl group having 1 to 10 carbon atoms and an aryl or alkylaryl group having 6 to 10 carbon atoms; Y is selected from the group consisting of $SO_3M^1$, $OSO_3M^1$, $(CH_2)_mSO_3M^1$, $(CH_2)_mOSO_3M^1$, $CO_2M^1$ and $N(R_7)_3X$; $R^7$ is selected from the group consisting of an alkyl group having 1 to 6 carbon atoms and a cycloalkyl group having 4 to 6 carbon atoms; X is a halogen atom; n is an integer from 1 to 10; and m is an integer from 1 to 2.

* * * * *